United States Patent
Ono et al.

(10) Patent No.: US 9,813,645 B2
(45) Date of Patent: Nov. 7, 2017

(54) IMAGE SENSOR, IMAGING DEVICE, ENDOSCOPE, AND ENDOSCOPIC SYSTEM

(71) Applicant: OLYMPUS CORPORATION, Tokyo (JP)

(72) Inventors: Makoto Ono, Sagamihara (JP); Nana Akahane, Yamanashi (JP); Masashi Saito, Akishima (JP); Yoshio Hagihara, Tokyo (JP); Susumu Yamazaki, Tachikawa (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 15/251,176

(22) Filed: Aug. 30, 2016

(65) Prior Publication Data
US 2016/0373666 A1 Dec. 22, 2016

Related U.S. Application Data

(63) Continuation of application No. PCT/JP2015/076145, filed on Sep. 15, 2015.

(30) Foreign Application Priority Data

Oct. 3, 2014 (JP) ................................. 2014-204820

(51) Int. Cl.
*A62B 1/04* (2006.01)
*H04N 5/357* (2011.01)
(Continued)

(52) U.S. Cl.
CPC ......... *H04N 5/357* (2013.01); *A61B 1/00009* (2013.01); *A61B 1/045* (2013.01);
(Continued)

(58) Field of Classification Search
CPC ............ H04N 5/357; H04N 2005/2255; A61B 1/045; A61B 1/05; A61B 1/00009; G02B 23/2484
(Continued)

(56) References Cited

U.S. PATENT DOCUMENTS

| 6,163,023 A | 12/2000 | Watanabe |
| 2007/0132868 A1* | 6/2007 | Lee .................... H03M 1/1019 348/308 |

(Continued)

FOREIGN PATENT DOCUMENTS

| JP | H11-177886 A | 7/1999 |
| JP | 2007-159115 A | 6/2007 |

OTHER PUBLICATIONS

International Search Report dated Dec. 22, 2015 issued in PCT/JP2015/076145.
(Continued)

*Primary Examiner* — Jared Walker
(74) *Attorney, Agent, or Firm* — Scully, Scott, Murphy & Presser, P.C.

(57) ABSTRACT

An image sensor includes: photoelectric conversion elements configured to receive light and accumulate a charge corresponding to an amount of received light; an imaging signal generating unit that converts the charge accumulated in each photoelectric conversion element into a voltage to generate an imaging signal; and a reference signal generating unit that generates a reference signal having a fluctuation component with a same phase as the imaging signal. The imaging signal generating unit includes: a conversion circuit that converts the charge accumulated in each photoelectric conversion element into the imaging signal; a noise eliminating circuit that eliminates a noise component included in the imaging signal; and an output circuit that outputs the imaging signal from the conversion circuit. The reference signal generating unit includes a circuit having a same structure as that of at least one of the conversion circuit, the noise eliminating circuit, and the output circuit.

9 Claims, 7 Drawing Sheets

(51) Int. Cl.
  *A61B 1/00* (2006.01)
  *A61B 1/05* (2006.01)
  *A61B 1/045* (2006.01)
  *G02B 23/24* (2006.01)
  *H04N 5/225* (2006.01)

(52) U.S. Cl.
  CPC ............ *A61B 1/05* (2013.01); *G02B 23/2484* (2013.01); *H04N 2005/2255* (2013.01)

(58) Field of Classification Search
  USPC .......................................................... 348/65
  See application file for complete search history.

(56) References Cited

U.S. PATENT DOCUMENTS

| | | |
|---|---|---|
| 2009/0160984 A1 | 6/2009 | Lee et al. |
| 2010/0271247 A1 | 10/2010 | Lee et al. |
| 2011/0054252 A1* | 3/2011 | Ozaki ................ A61B 1/00089 600/109 |

OTHER PUBLICATIONS

Japanese Office Action dated Apr. 12, 2016 issued in JP 2016-504831.

\* cited by examiner

IMAGE SENSOR, IMAGING DEVICE, ENDOSCOPE, AND ENDOSCOPIC SYSTEM

CROSS-REFERENCE TO RELATED APPLICATIONS

This application is a continuation of PCT international application Ser. No. PCT/JP2015/076145 filed on Sep. 15, 2015 which designates the United States, incorporated herein by reference, and which claims the benefit of priority from Japanese Patent Application No. 2014-204820, filed on Oct. 3, 2014, incorporated herein by reference.

BACKGROUND

1. Technical Field

The disclosure relates to an image sensor configured to image a subject to generate image data of the subject. The disclosure also relates to an imaging device, an endoscope, and an endoscopic system.

2. Related Art

Conventionally, image sensors such as a CMOS (Complementary Metal-Oxide Semiconductor) image sensor hold an image signal transferred row by row using a sample-and-hold circuit, sequentially output the image signal to a horizontal output signal line for each pixel using column reading circuit, and perform reading of the image signal. In such image sensors, a technique has been known which provides a reference voltage generator to generate a reference voltage signal in the image sensor and acquires a difference between the reference voltage signal and an image signal using an analog front end circuit (hereinafter, referred to the "AFE circuit") provided outside the image sensor in order to reduce a fixed pattern noise of an image sensor (see JP 2007-159115 A).

SUMMARY

In some embodiments, an image sensor includes: a plurality of photoelectric conversion elements arranged in a two-dimensional matrix form, each of the plurality of photoelectric conversion elements being configured to receive light from outside and accumulate a charge corresponding to an amount of received light; an imaging signal generating unit configured to convert the charge accumulated in each of the plurality of photoelectric conversion elements into a voltage to generate an imaging signal; and a reference signal generating unit configured to generate a reference signal having a fluctuation component with a same phase as the imaging signal generated by the imaging signal generating unit. The imaging signal generating unit includes: a conversion circuit configured to convert the charge accumulated in each of the plurality of photoelectric conversion elements into the imaging signal; a noise eliminating circuit configured to eliminate a noise component included in the imaging signal; and an output circuit configured to output the imaging signal from the conversion circuit. The reference signal generating unit includes a circuit having a same structure as that of at least one of the conversion circuit, the noise eliminating circuit, and the output circuit.

In some embodiments, an imaging device includes the image sensor.

In some embodiments, an endoscope includes the imaging device at a distal end side of an insertion portion.

In some embodiments, an endoscopic system includes: the endoscope, and a processing device configured to perform conversion into an image signal using the imaging signal and the reference signal.

The above and other features, advantages and technical and industrial significance of this invention will be better understood by reading the following detailed description of presently preferred embodiments of the invention, when considered in connection with the accompanying drawings.

DETAILED DESCRIPTION

Hereinafter, reference will be made to an endoscopic system having an imaging device as modes for carrying out the present invention (hereinafter, referred to as "embodiment(s)"). The present invention is not limited to the embodiments. The same reference signs are used to designate the same elements throughout the drawings. Note that the drawings are schematic, and a relation between a thickness and a width of each member, each ratio of the members, and the like are differ from the actual ones. Portions that have different sizes and ratios may be included among the drawings.

First Embodiment

Configuration of Endoscopic System

Figure 1:
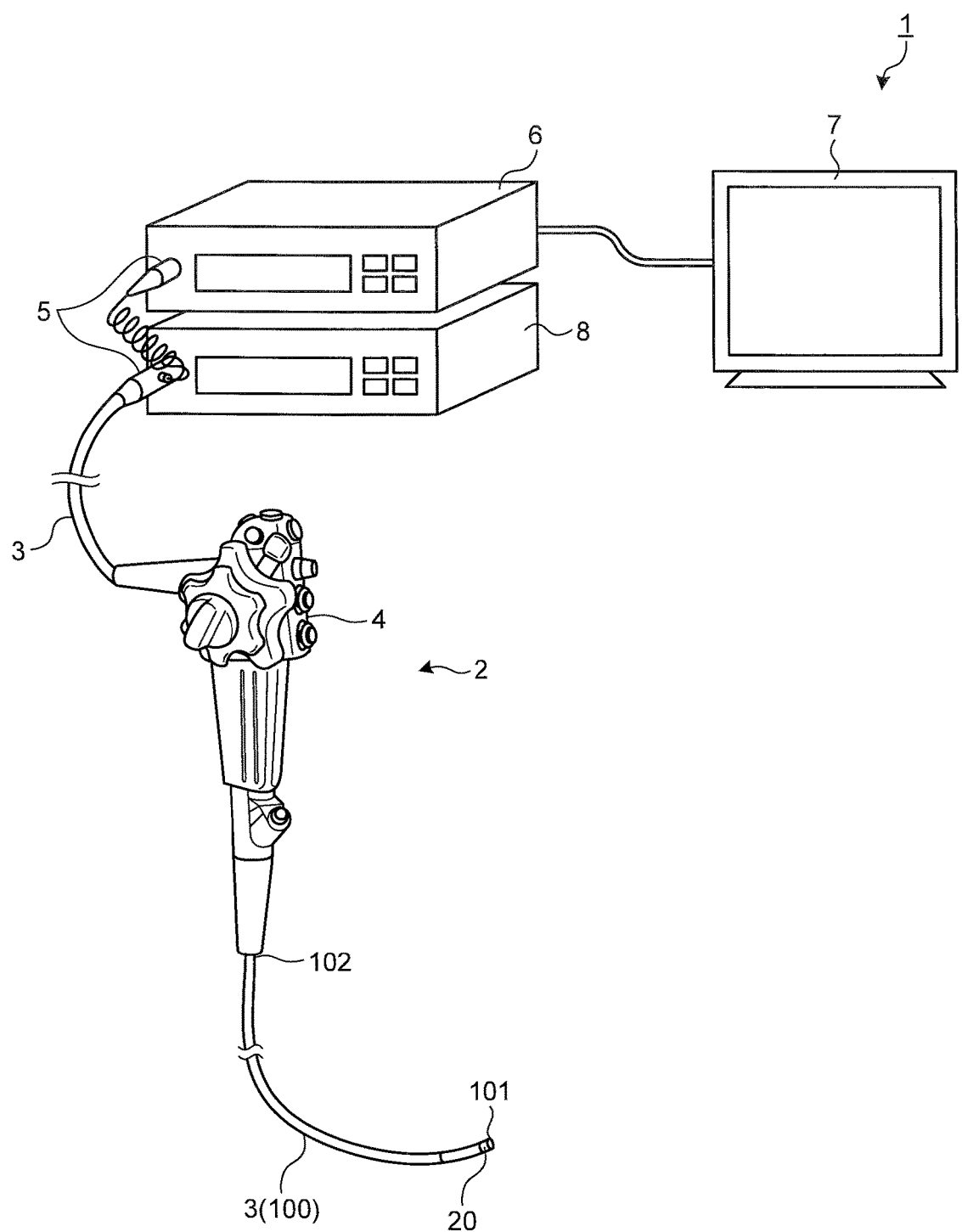
FIG. 1 is a diagram schematically illustrating an overall configuration of an endoscopic system according to a first embodiment of the present invention.

FIG. 1 is a diagram schematically illustrating an overall configuration of an endoscopic system according to a first embodiment of the present invention. An endoscopic system 1 illustrated in FIG. 1 is provided with an endoscope 2, a transmission cable 3, a connector unit 5, a processor 6 (processing device), a display device 7, and a light source device 8.

The endoscope 2 captures an in-vivo image of a subject by inserting an insertion portion 100, which is a part of the transmission cable 3, into a body cavity of the subject, and outputs an imaging signal (image data) to the processor 6. In addition, the endoscope 2 is provided with an imaging unit 20 (imaging device), which captures the in-vivo image on one end side of the transmission cable 3, that is, on a distal end 101 of the insertion portion 100 to be inserted into the body cavity of the subject, and an operating unit 4 that receives various operations for the endoscope 2 is connected to a proximal end 102 of the insertion portion 100. The imaging unit 20 is connected to the connector unit 5 via the operating unit 4 using the transmission cable 3. The imaging signal of an image captured by the imaging unit 20 is output to the connector unit 5 through the transmission cable 3 having a length of a few meters, for example.

The connector unit 5 is connected to the endoscope 2, the processor 6, and the light source device 8, performs predetermined signal processing on the imaging signal output from the connected endoscope 2, performs conversion (A/D conversion) of the imaging signal from an analog signal to a digital signal, and outputs the converted signal to the processor 6 as an image signal.

The processor 6 performs predetermined image processing on the image signal output from the connector unit 5, and comprehensively controls the entire endoscopic system 1. The processor 6 functions as a processing device in the first embodiment.

The display device 7 displays an image corresponding to the image signal that has been subjected to the image processing by the processor 6. In addition, the display device 7 displays various types of information relating to the endoscopic system 1.

The light source device 8 is configured using, for example, a halogen lamp, a white LED (Light Emitting Diode) or the like, and allows the subject to be irradiated with illumination light from the distal end 101 side of the insertion portion 100 of the endoscope 2 via the connector unit 5 and the transmission cable 3.

Figure 2:
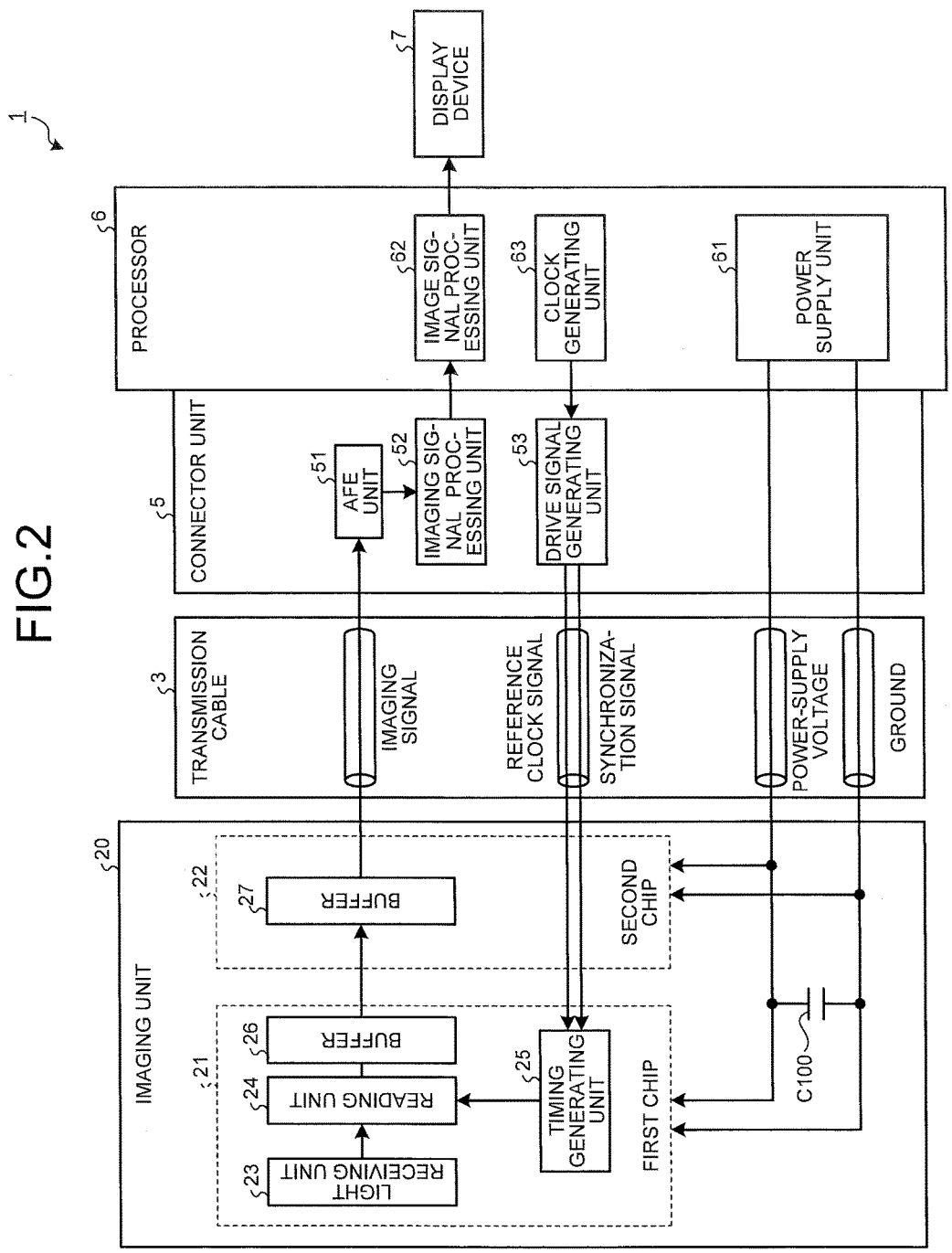
FIG. 2 is a block diagram illustrating a function of the main part of the endoscopic system according to the first embodiment of the present invention.

FIG. 2 is a block diagram illustrating a function of the main part of the endoscopic system 1. A description will be given regarding details of configurations of the respective units of the endoscopic system 1 and a route of an electrical signal inside the endoscopic system 1 with reference to FIG. 2.

As illustrated in FIG. 2, the imaging unit 20 is provided with a first chip 21 (image sensor) and a second chip 22.

The first chip 21 includes a light receiving unit 23 in which a plurality of unit pixels are arranged in a two-dimensional matrix form in row and column directions, a reading unit 24 which reads the imaging signal which has been photoelectrically converted by the light receiving unit 23, a timing generating unit 25 which generates a timing signal based on a reference clock signal and a synchronization signal input from the connector unit 5 and outputs the timing signal to the reading unit 24, and a buffer 26 which temporarily holds the imaging signal and a reference signal that are read by the reading unit 24 from the light receiving unit 23. A more detailed configuration of the first chip 21 will be described later with reference to FIG. 3.

The second chip 22 includes a buffer 27 which functions as a transmitting unit that transmits the imaging signal output from the first chip 21 to the processor 6 via the transmission cable 3 and the connector unit 5. Combinations of circuits to be mounted on the first chip 21 and the second chip 22 may be changed as appropriate according to design conditions.

In addition, the imaging unit 20 receives a power-supply voltage VDD, which is generated by a power supply unit 61 inside the processor 6, together with ground GND via the transmission cable 3. A capacitor C100 for power supply stabilization is provided between the power-supply voltage VDD and the ground GND to be supplied to the imaging unit 20.

The connector unit 5 includes an analog front end unit 51 (hereinafter, referred to as the "AFE unit 51"), an imaging signal processing unit 52, and a drive signal generating unit 53. The connector unit 5 functions as a relay processing unit that electrically connects the endoscope 2 (the imaging unit 20) and the processor 6, and relays an electrical signal. The connector unit 5 and the imaging unit 20 are connected using the transmission cable 3, and the connector unit 5 and the processor 6 are connected using a coil cable. In addition, the connector unit 5 is connected also to the light source device 8.

The AFE unit 51 receives the imaging signal transmitted from the imaging unit 20, and performs impedance matching by a passive element, such as a resistance, and then, takes out an alternating current component by a capacitor and determines an operating point by a partial resistance. Thereafter, the AFE unit 51 performs the A/D conversion on an analog imaging signal that has been transmitted from the imaging unit 20, and outputs the converted signal to the imaging signal processing unit 52 as a digital imaging signal.

The imaging signal processing unit 52 performs predetermined signal processing, such as vertical line elimination and noise elimination, with respect to the digital imaging signal input from the AFE unit 51, and outputs the processed signal to the processor 6. The imaging signal processing unit 52 is configured using, for example, a FPGA (Field Programmable Gate Array).

The drive signal generating unit 53 generates a synchronization signal indicating a start position of each frame based on the reference clock signal (for example, a clock signal of 27 MHz), which is supplied from the processor 6 and serves as a reference of operation of each component of the endoscope 2, and outputs the generated synchronization signal to the timing generating unit 25 of the imaging unit 20 together with the reference clock signal via the transmission cable 3. Here, the synchronization signal generated by the drive signal generating unit 53 includes a horizontal synchronization signal and a vertical synchronization signal.

The processor 6 is a control device that comprehensively controls the entire endoscopic system 1. The processor 6 is provided with a power supply unit 61, an image signal processing unit 62, and a clock generating unit 63.

The power supply unit 61 generates the power-supply voltage VDD, and supplies the generated power-supply voltage VDD to the imaging unit 20 together with the ground GND via the connector unit 5 and the transmission cable 3.

The image signal processing unit 62 performs image processing such as a synchronization process, a white balance (WB) adjustment process, a gain adjustment process, a gamma correction process, a digital-analog (D/A) conversion process, or a format conversion process, on the digital imaging signal, which has been subjected to the signal processing by the imaging signal processing unit 52, converts the processed signal into an image signal, and outputs the image signal to the display device 7.

The clock generating unit 63 generates the reference clock signal serving as the reference of operation of each component of the endoscopic system 1, and outputs the reference clock signal to the drive signal generating unit 53.

The display device 7 displays the image captured by the imaging unit 20 based on the image signal which is input from the image signal processing unit 62. The display device 7 is configured using a display panel and the like of liquid crystal or organic EL (Electro Luminescence).

Configuration of First Chip

Next, a detailed configuration of the above-described first chip 21 will be described.

Figure 3:
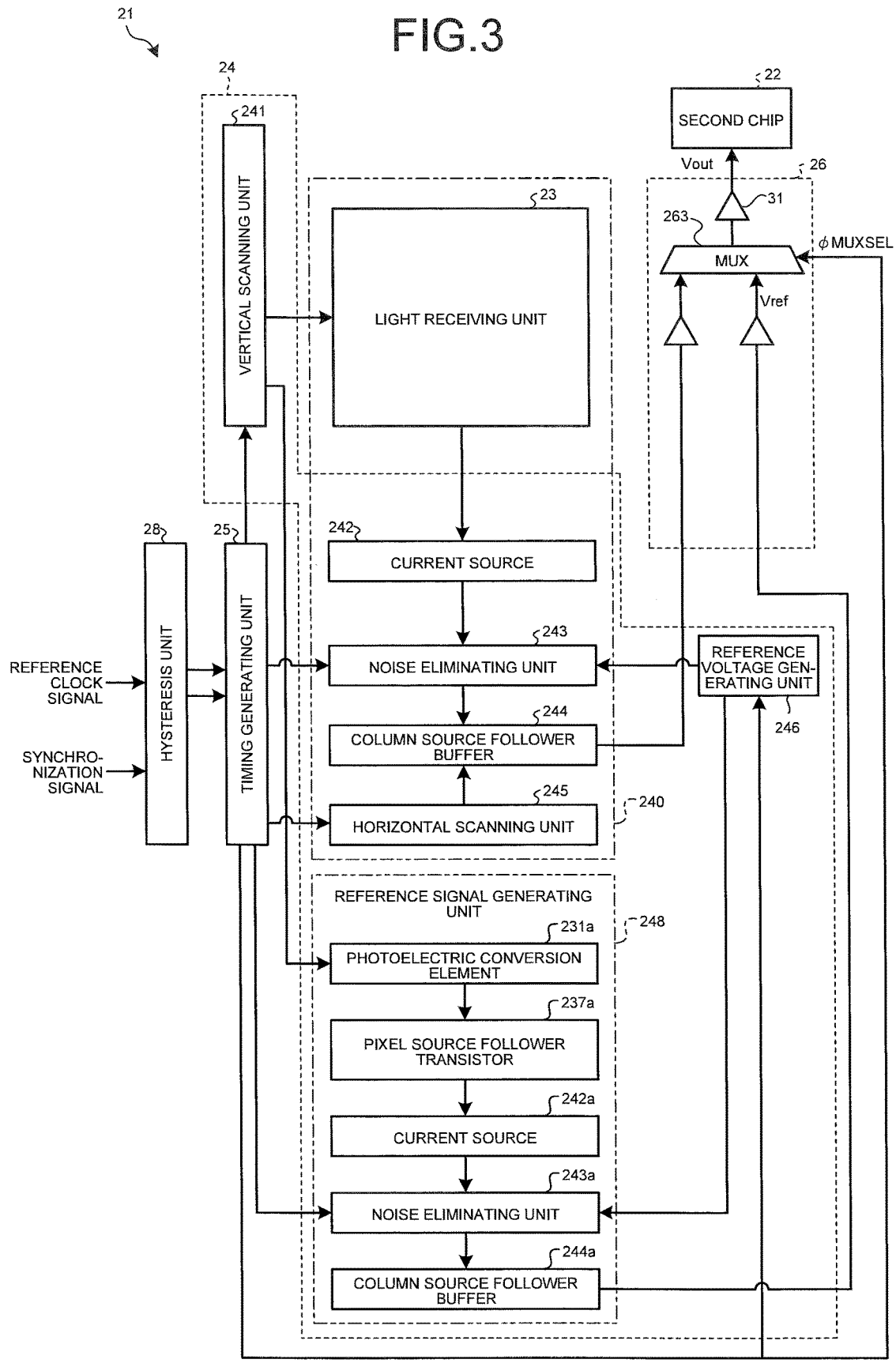
FIG. 3 is a block diagram illustrating a detailed configuration of a first chip of an imaging unit in the endoscopic system according to the first embodiment of the present invention.
Figure 4:
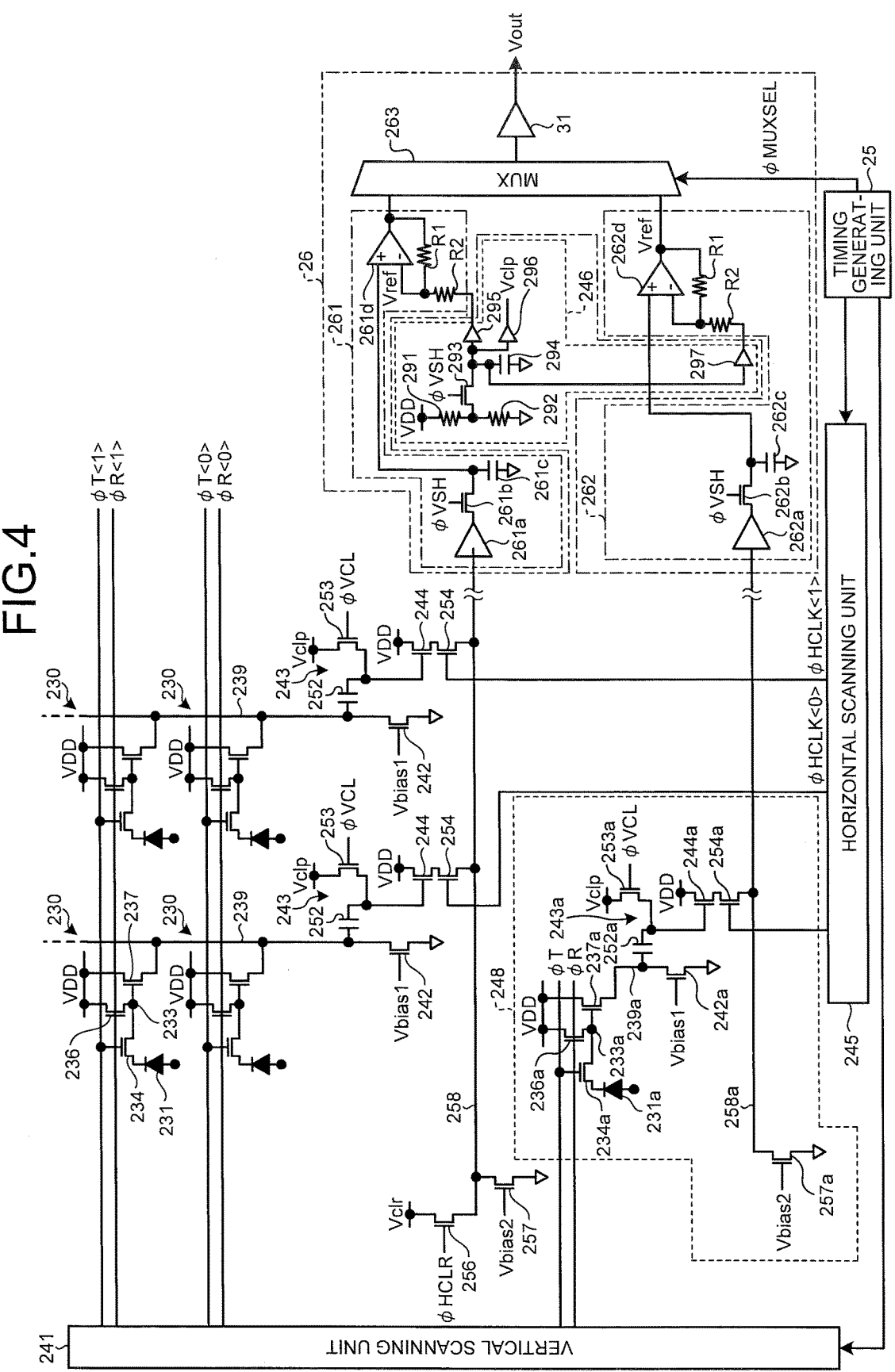
FIG. 4 is a circuit diagram illustrating the configuration of the first chip of the imaging unit in the endoscopic system according to the first embodiment of the present invention.

FIG. 3 is a block diagram illustrating the detailed configuration of the first chip 21 illustrated in FIG. 2. FIG. 4 is a circuit diagram illustrating the configuration of the first chip 21.

As illustrated in FIGS. 3 and 4, the first chip 21 includes the light receiving unit 23, the reading unit 24 (drive unit), the timing generating unit 25, the buffer 26, and a hysteresis unit 28.

The hysteresis unit 28 performs waveform shaping on the reference clock signal and the synchronization signal input via the transmission cable 3, and outputs the reference clock signal and the synchronization signal that have been subjected to the waveform shaping to the timing generating unit 25.

The timing generating unit 25 generates various drive signals based on the reference clock signal and the synchronization signal input from the hysteresis unit 28, and outputs the generated drive signals to a vertical scanning unit 241 (row selection circuit), a noise eliminating unit 243 and a horizontal scanning unit 245 of the reading unit 24, which will be described later, a noise eliminating unit 243a of a reference signal generating unit 248, which will be described later, and a multiplexer 263 of the buffer 26 which will be described later.

The reading unit 24 transfers an imaging signal which is output from each of a plurality of pixels, which will be described later, of the light receiving unit 23, and the reference signal which is output from the reference signal generating unit 248 in different periods.

Here, a detailed configuration of the reading unit 24 will be described. The reading unit 24 includes the vertical scanning unit 241 (row selection circuit), a current source 242, the noise eliminating unit 243 (noise eliminating circuit), a column source follower buffer 244, the horizontal scanning unit 245, a reference voltage generating unit 246, and the reference signal generating unit 248.

The vertical scanning unit 241 applies row selection pulses φT<M> and φR<M> to a selected row <M> (M=0, 1, 2 . . . , m−1, m) of the light receiving unit 23 based on a drive signal φT, φR or the like) input from the timing generating unit 25 to cause each unit pixel 230 of the light receiving unit 23 to be driven by the current source 242, transfers an imaging signal and a noise signal at the time of pixel resetting to a vertical transfer line 239 (first transfer line), and outputs the signals to the noise eliminating unit 243 and the noise eliminating unit 243a of the reference signal generating unit 248, which will be described later.

The noise eliminating unit 243 eliminates output variations of the respective unit pixel 230 and the noise signal at the time of pixel resetting, and outputs the imaging signal which has been photoelectrically converted by each of the unit pixels 230. Details of the noise eliminating unit 243 will be described later.

The horizontal scanning unit 245 applies a column selection pulse φHCLK(N) to a selected column <N> (N=0, 1, 2 . . . , n−1, n) of the light receiving unit 23 based on a drive signal (φHCLK) supplied from the timing generating unit 25, transfers the imaging signal, which has been photoelectrically converted by each of the unit pixels 230, to a horizontal transfer line 258 (second transfer line) via the noise eliminating unit 243, and outputs the signal to the buffer 26.

The light receiving unit 23 of the first chip 21 includes the multiple unit pixels 230 (photoelectric conversion units) which are arrayed in a two-dimensional matrix form, and a plurality of photoelectric conversion elements 231 each of which receives light from outside and accumulates a charge corresponding to the amount of received light. Each of the unit pixels 230 includes the photoelectric conversion element 231 (photodiode), a charge converter 233, a transfer transistor 234 (first transfer unit), a pixel resetting unit 236 (transistor), and a pixel source follower transistor 237 (voltage conversion circuit). One or the plurality of photoelectric conversion elements and the transfer transistor, which is configured to transfer a signal charge from each photoelectric conversion element to the charge converter 233 are called a unit cell in the first embodiment. That is, the unit cell includes a set of one or the plurality of photoelectric conversion elements and the transfer transistor, and each of the unit pixels 230 includes one unit cell. In addition, a circuit which is configured of the light receiving unit 23 (the photoelectric conversion element 231), the current source 242, the noise eliminating unit 243, the column source follower buffer 244, and the horizontal scanning unit 245, functions as an imaging signal generating unit 240 that converts the charge accumulated in each of the plurality of photoelectric conversion elements 231 into a voltage to generate an imaging signal.

The photoelectric conversion element 231 photoelectrically converts incident light into a signal charge amount corresponding to the amount of light, and accumulates the signal charge amount. The photoelectric conversion element 231 has a cathode side being connected to one end side of the transfer transistor 234 and an anode side being connected to the ground GND.

The charge converter 233 is formed of a floating diffusion capacitor (FD), and converts the charge accumulated in the photoelectric conversion element 231 into a voltage.

The transfer transistor 234 transfers the charge from the photoelectric conversion element 231 to the charge converter 233. The transfer transistor 234 has a gate being connected with a signal line to which the drive signal φT is supplied, and the other end side being connected to the charge converter 233. The transfer transistor 234 is turned into an ON state when the drive signal φT is supplied from the vertical scanning unit 241 via the signal line, and transfers the signal charge from the photoelectric conversion element 231 to the charge converter 233.

The pixel resetting unit 236 (transistor) resets the charge converter 233 to a predetermined potential. The pixel resetting unit 236 has one end side being connected to the power-supply voltage VDD and the other end side being connected to the charge converter 233, and a gate thereof is connected with a signal line to which the drive signal φR is supplied. The pixel resetting unit 236 is turned into an ON state when the drive signal φR is supplied from the vertical scanning unit 241 via the signal line, and releases the signal charge accumulated in the charge converter 233 and resets the charge converter 233 to a predetermined potential.

The pixel source follower transistor 237 (the conversion circuit) has one end side being connected to the power-supply voltage VDD and the other end side being connected to the vertical transfer line 239, and a signal (an imaging signal or a signal at the time of resetting), which has been subjected to voltage conversion in the charge converter 233, is input to a gate thereof. The pixel source follower transistor 237 reads the charge from the photoelectric conversion element 231 when the drive signal φT is supplied to the gate of the transfer transistor 234, and transfers the imaging signal after being subjected to the voltage conversion in the charge converter 233 to the vertical transfer line 239. The pixel source follower transistor 237 functions as a conversion circuit that converts the charge accumulated in each of the plurality of photoelectric conversion elements into the imaging signal in the first embodiment.

The current source 242 has one end side being connected to the vertical transfer line 239 and the other end side being connected to the ground GND, and a bias voltage Vbias1 is applied to a gate thereof. The unit pixel 230 is driven by the current source 242, and the output (imaging signal) of the unit pixel 230 is read to the vertical transfer line 239. The signal (imaging signal) that has been read to the vertical transfer line 239 is input to the noise eliminating unit 243.

The noise eliminating unit 243 includes a transfer capacitor 252 (AC coupling capacitor) and a clamp switch 253 (transistor). The transfer capacitor 252 has one end side being connected to the vertical transfer line 239 and the other end side being connected to the column source follower buffer 244. The clamp switch 253 has one end side being connected to a signal line to which a clamp voltage Vclp is supplied from the reference voltage generating unit 246 and the other end side being connected between the transfer capacitor 252 and the column source follower buffer 244, and a drive signal ϕVCL is supplied to a gate thereof from the timing generating unit 25. The imaging signal input to the noise eliminating unit 243 includes a noise component. In the first embodiment, the noise eliminating unit 243 functions as a noise eliminating circuit.

When the drive signal ϕVCL is input from the timing generating unit 25 to the gate of the clamp switch 253 in the noise eliminating unit 243, the clamp switch 253 is turned into the ON state, and the transfer capacitor 252 is reset by the clamp voltage Vclp supplied from the reference voltage generating unit 246. The imaging signal from which noise is eliminated by the noise eliminating unit 243 is input to the gate of the column source follower buffer 244.

The noise eliminating unit 243 does not require a capacitor for sampling (sampling capacitor), and thus, it is enough when a capacitance of the transfer capacitor 252 (AC coupling capacitor) is a capacitance sufficient with respect to an input capacitance of the column source follower buffer 244. Further, it is possible to reduce an area occupied by the first chip 21 as the sampling capacitor is not provided in the noise eliminating unit 243.

The column source follower buffer 244 has one end side being connected to the power-supply voltage VDD and the other end side being connected to one end side of a column selection switch 254 (second transfer unit), and an imaging signal is input to a gate thereof via the noise eliminating unit 243.

The column selection switch 254 has one end side being connected to the other end side of the column source follower buffer 244 and the other end side being connected to the horizontal transfer line 258 (second transfer line), and a signal line, which is configured to supply a drive signal (column selection pulse) ϕHCLK<N> from the horizontal scanning unit 245, is connected to a gate thereof. The column selection switch 254 is turned into an ON state when the drive signal ϕHCLK<N> is supplied to the gate from the horizontal scanning unit 245, and transfers (outputs) the signal (imaging signal) of the vertical transfer line 239 of the column <N> to the horizontal transfer line 258. The column source follower buffer 244 and the column selection switch 254 function as output circuits that output the imaging signal from the pixel source follower transistor 237 in the first embodiment.

A horizontal resetting transistor 256 has one end side being connected to a horizontal reset voltage Vclr and the other end side being connected to the horizontal transfer line 258, and a drive signal ϕHCLR is input to a gate thereof from the timing generating unit 25. The horizontal resetting transistor 256 is turned into an ON state when the drive signal ϕHCLR is input to the gate from the timing generating unit 25, and resets the horizontal transfer line 258.

A constant current source 257 has one end side being connected to the horizontal transfer line 258 and the other end side being connected to the ground GND, and a bias voltage Vbias2 is applied to a gate thereof. The column source follower buffer 244 is driven by the constant current source 257, and a signal (imaging signal) is read from the vertical transfer line 239 to the horizontal transfer line 258. The signal (imaging signal) that has been read to the horizontal transfer line 258 is input to and held in the buffer 26.

The reference signal generating unit 248 is connected to a dedicated vertical transfer line 239a separately from a column of the unit pixel 230. The reference signal generating unit 248 includes a circuit that generates a reference signal having a fluctuation component with the same phase as a fluctuation component of the power supply existing in the output signal (imaging signal) to be formed by the imaging signal generating unit 240. To be specific, the reference signal generating unit 248 includes the circuit which has a structure equivalent to at least one or more circuits among a plurality of circuits configuring the imaging signal generating unit 240.

Here, a detailed configuration of the reference signal generating unit 248 will be described. The reference signal generating unit 248 includes a photoelectric conversion element 231a (dummy photodiode), a charge converter 233a, a transfer transistor 234a, a pixel resetting unit 236a, a pixel source follower transistor 237a, a current source 242a, the noise eliminating unit 243a, a column source follower buffer 244a, and a column selection switch 254a.

The photoelectric conversion element 231a has the same configuration as the above-described photoelectric conversion element 231, and photoelectrically converts incident light into a signal charge amount corresponding to the amount of light and accumulates the signal charge amount. The photoelectric conversion element 231a has a cathode side being connected to one end side of the transfer transistor 234a and the anode side being connected to the ground GND.

The charge converter 233a has the same configuration as the above-described charge converter 233a, and converts the charge accumulated in the photoelectric conversion element 231a into a voltage.

The transfer transistor 234a has the same configuration as the above-described transfer transistor 234, and transfers the charge to the charge converter 233a from the photoelectric conversion element 231a. The transfer transistor 234a has a gate being connected with a signal line to which the drive signal ϕT is supplied, and the other end side being connected to the charge converter 233a. The transfer transistor 234a is turned into an ON state when the drive signal ϕT is supplied from the vertical scanning unit 241 via the signal line, and transfers the signal charge from the photoelectric conversion element 231a to the charge converter 233a.

The pixel resetting unit 236a has the same configuration as the above-described pixel resetting unit 236, and resets the charge converter 233a to a predetermined potential. The pixel resetting unit 236a has one end side being connected to the power-supply voltage VDD and the other end side being connected to the charge converter 233a, and a gate thereof is connected with a signal line to which the drive signal ϕR is supplied. The pixel resetting unit 236a is turned into an ON state when the drive signal ϕR is supplied from the vertical scanning unit 241 via the signal line, and the signal charge accumulated in the charge converter 233a is released to reset the charge converter 233a to a predetermined potential.

The pixel source follower transistor 237a has the same configuration as the above-described pixel source follower transistor 237. The pixel source follower transistor 237a has one end side being connected to the power-supply voltage VDD and the other end side being connected to the vertical transfer line 239a, and a signal (reference signal) whose voltage has been converted by the charge converter 233a, is input to a gate thereof. When the drive signal φT is supplied to the gate of the transfer transistor 234a, the pixel source follower transistor 237a reads the charge from the photoelectric conversion element 231a, and transfers the reference signal after being subjected to the voltage conversion by the charge converter 233a, to the vertical transfer line 239a.

The current source 242a has the same configuration as the above-described current source 242. The current source 242a has one end side being connected to the vertical transfer line 239a and the other end side being connected to the ground GND, and the bias voltage Vbias1 is applied to a gate thereof. The photoelectric conversion element 231a is driven by the current source 242a, and the output (reference signal) of the photoelectric conversion element 231a is read to the vertical transfer line 239a. The signal (reference signal) that has been read to the vertical transfer line 239a is input to the noise eliminating unit 243a.

The noise eliminating unit 243a has the same configuration as the above-described noise eliminating unit 243, and includes a transfer capacitor 252a (AC coupling capacitor) and a clamp switch 253a (transistor). The transfer capacitor 252a has one end side being connected to the vertical transfer line 239a and the other end side being connected to the column source follower buffer 244a. The clamp switch 253a has one end side being connected to a signal line to which the clamp voltage Vclp is supplied from the reference voltage generating unit 246 and the other end side being connected between the transfer capacitor 252a and the column source follower buffer 244a, and the drive signal φVCL is input to a gate thereof from the timing generating unit 25. The reference signal input to the noise eliminating unit 243a includes a noise component.

When the drive signal φVCL is input from the timing generating unit 25 to the gate of the clamp switch 253a in the noise eliminating unit 243a, the clamp switch 253a is turned into the ON state, and the transfer capacitor 252a is reset by the clamp voltage Vclp supplied from the reference voltage generating unit 246. The reference signal from which noise is eliminated by the noise eliminating unit 243a is input to the gate of the column source follower buffer 244a.

The column source follower buffer 244a has the same configuration as the above-described column source follower buffer 244. The column source follower buffer 244a has one end side being connected to the power-supply voltage VDD and the other end side being connected to one end side of the column selection switch 254a, and the reference signal is input to a gate thereof via the noise eliminating unit 243a.

The column selection switch 254a has the same configuration as the above-described column selection switch 254. The column selection switch 254a has one end being connected to the other end side of the column source follower buffer 244a and the other end side being connected to a horizontal transfer line 258a, and a signal line, which is configured to supply the drive signal φCLK<N> from the horizontal scanning unit 245, is connected to a gate thereof.

The column selection switch 254a is turned into an ON state when the drive signal φHCLK<N> is supplied to the gate from the horizontal scanning unit 245, and transfers the signal (reference signal) of the vertical transfer line 239a to the horizontal transfer line 258a.

A constant current source 257a has the same configuration as the above-described constant current source 257. The constant current source 257a has one end side being connected to the horizontal transfer line 258a and the other end side being connected to the ground GND, and the bias voltage Vbias2 is applied to a gate thereof. The column source follower buffer 244a is driven by the constant current source 257a, and the reference signal is read from the vertical transfer line 239a to the horizontal transfer line 258a. The reference signal that has been red to the horizontal transfer line 258a is input to and held in the buffer 26.

In this manner, the reference signal generating unit 248 includes an element or a circuit which has a structure equivalent to at least one of a plurality of circuits or elements included in the imaging signal generating unit 240. To be specific, the reference signal generating unit 248 includes the element or the circuit which has the equivalent structure, for example, the photoelectric conversion element 231a, the charge converter 233a, the transfer transistor 234a, the pixel resetting unit 236a, the pixel source follower transistor 237a, the current source 242a, the noise eliminating unit 243a, the column source follower buffer 244a, and the column selection switch 254a among the photoelectric conversion element 231, the charge converter 233, the transfer transistor 234, the pixel resetting unit 236, the pixel source follower transistor 237, the current source 242, the noise eliminating unit 243, the column source follower buffer 244, and the column selection switch 254 configuring the imaging signal generating unit 240.

The reference voltage generating unit 246 includes a resistance voltage dividing circuit, formed of two resistance 291 and resistance 292, a switch 293 driven using the drive signal φVSH, a sampling capacitor 294, an operational amplifier 295, an operational amplifier 296, and an operational amplifier 297. The reference voltage generating unit 246 generates a reference signal voltage $Vfd_{13}$ H from the power-supply voltage VDD and the clamp voltage Vclp of the noise eliminating unit 243 at a timing that the drive signal φVSH is driven by driving of the switch 293.

The buffer 26 holds the imaging signal input from the horizontal transfer line 258 and the reference signal (Vref) input from the horizontal transfer line 258a individually, and outputs the imaging signal and the reference signal to the second chip 22 in a sequentially switched manner based on a signal (drive signal φMUXSEL) input from the timing generating unit 25.

Here, a detailed configuration of the buffer 26 will be described. The buffer 26 includes a first sampling and holding unit 261, a second sampling and holding unit 262, the multiplexer 263, and an output buffer 31.

The first sampling and holding unit 261 includes a first buffer 261a, a first sampling and holding switch 261b, a first sampling capacitor 261c, and a first operational amplifier 261d.

The horizontal transfer line 258 is connected to an input side of the first buffer 261a, and the first sampling and holding switch 261b is connected to an output side thereof. The imaging signal and the horizontal resetting voltage (Vclr) are input to the first buffer 261a via the horizontal transfer line 258.

The first sampling and holding switch 261b has one end side being connected to the output side of the first buffer 261a, the other end side being connected to an input side (plus terminal) of the first operational amplifier 261d, and a gate being connected with a signal line to which the drive signal ϕVSH is supplied.

The first sampling capacitor 261c has one end side being connected to the other end side of the first sampling and holding switch 261b and the other end side being connected to the ground GND.

The input side (plus terminal) of the first operational amplifier 261d is connected to the other end side of the first sampling and holding switch 261b, and an output side thereof is connected to the multiplexer 263. In addition, the output of the first operational amplifier 261d is input to an inverting input terminal (minus terminal) of the first operational amplifier 261d via a resistance R1. Further, the reference signal voltage Vfd_H is input to the inverting input terminal (minus terminal) of the first operational amplifier 261d from the reference voltage generating unit 246 via a resistance R2.

The first sampling and holding unit 261 configured in this manner holds a voltage immediately before the first sampling and holding switch 261b is turned into an ON state in the first sampling capacitor 261c, and outputs the voltage held in the first sampling capacitor 261c to the multiplexer 263 while the first sampling and holding switch 261b is in an OFF state.

The second sampling and holding unit 262 includes a second buffer 262a, a second sampling and holding switch 262b, a second sampling capacitor 262c, and a second operational amplifier 262d.

The horizontal transfer line 258a is connected to an input side of the second buffer 262a, and the second sampling and holding switch 262b is connected to an output side thereof. The reference signal is input to the second buffer 262a via the horizontal transfer line 258a.

The second sampling and holding switch 262b has one end side being connected to the output side of the second buffer 262a, the other end side being connected to an input side (plus terminal) of the second operational amplifier 262d, and a gate being connected with a signal line to which the drive signal ϕVSH is supplied.

The second sampling capacitor 262c has one end side being connected to the other end side of the second sampling and holding switch 262b and the other end side being connected to the ground GND.

The input side (plus terminal) of the second operational amplifier 262d is connected to the other end side of the second sampling and holding switch 262b, and an output side thereof is connected to the multiplexer 263. In addition, the output of the second operational amplifier 262d is input to an inverting input terminal (minus terminal) of the second operational amplifier 262d via the resistance R1. Further, the reference signal voltage Vfd_H is input to the inverting input terminal (minus terminal) of the second operational amplifier 262d from the reference voltage generating unit 246 via a resistance R2.

The second sampling and holding unit 262 configured in this manner holds a voltage immediately before the second sampling and holding switch 262b is turned into an ON state in the second sampling capacitor 262c, and outputs the voltage held in the second sampling capacitor 262c to the multiplexer 263 while the second sampling and holding switch 262b is in an OFF state.

The multiplexer 263 outputs the imaging signal input from the first sampling and holding unit 261 and the reference signal input from the second sampling and holding unit 262 to the output buffer 31 in a switched manner based on the drive signal ϕMUXSEL input from the timing generating unit 25.

The output buffer 31 performs signal amplification on the imaging signal and the reference signal (reference voltage Vref) from which noise is eliminated if necessary, and alternately outputs the amplified signals to the second chip 22.

The second chip 22 transmits each reference signal having a fluctuation component with the same phase as an imaging signal and an imaging signal from which the noise components are eliminated to the connector unit 5 via the transmission cable 3.

Operation of Imaging Unit

Figure 5:
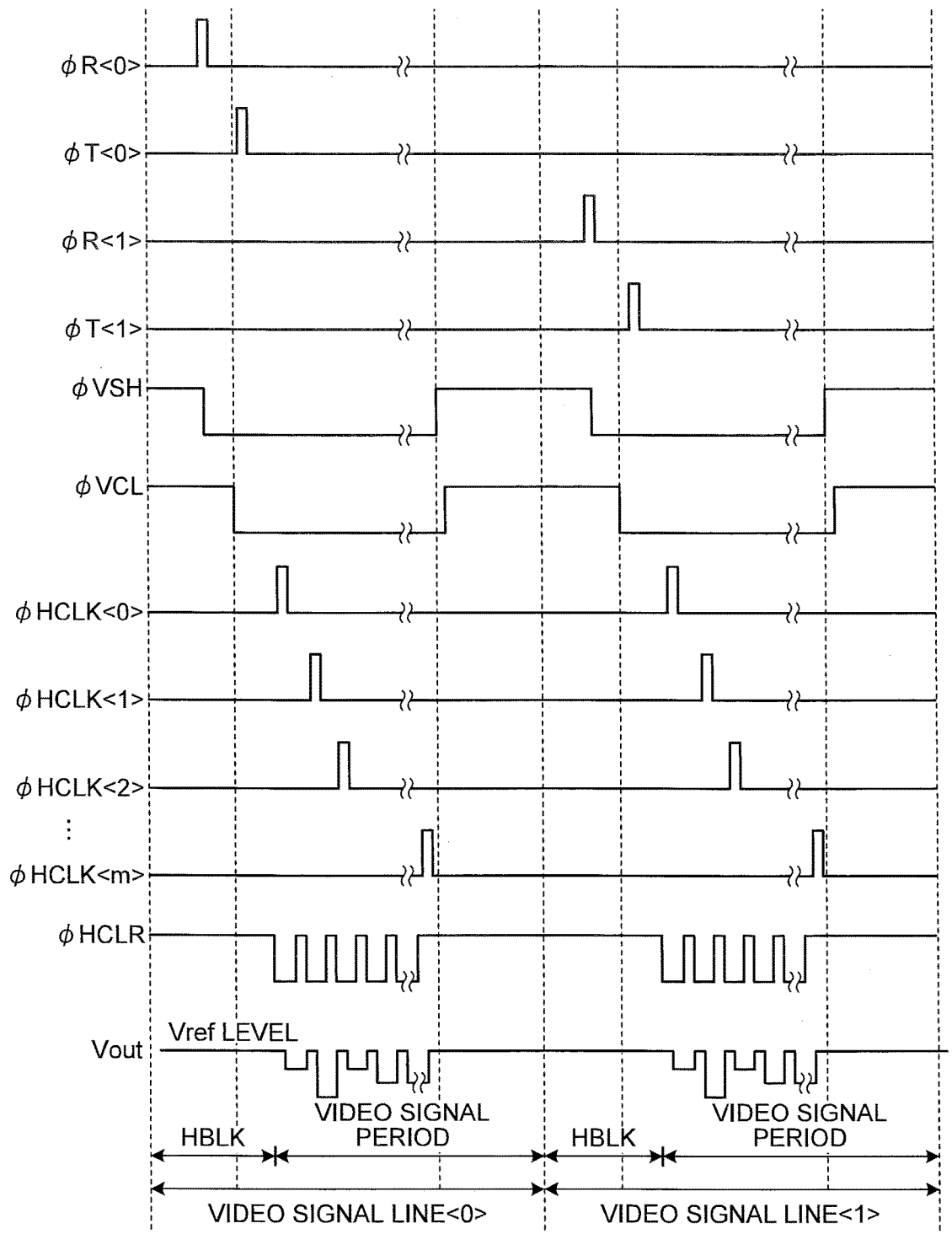
FIG. 5 is a timing chart illustrating a drive signal of the imaging unit in the endoscopic system according to the first embodiment of the present invention.

Next, a drive timing of the imaging unit 20 will be described. FIG. 5 is a timing chart illustrating a drive signal of the imaging unit 20. FIG. 5 describes a state between reading of signals from the unit pixels 230 of the row <0> and the row <1> of the light receiving unit 23 and outputting thereof through the output buffer 31. In addition, it is assumed that only the photoelectric conversion element 231 is included in the unit pixel 230 in the timing chart illustrated in FIG. 5 for the purpose of explanation. In a case where the plurality of photoelectric conversion elements are included in the unit pixel 230, the operation for a single video signal line illustrated in the timing chart is repeatedly performed as many times as the number of the photoelectric conversion elements 231 included in the unit pixel 230. FIG. 5 illustrates the drive signals ϕR, ϕT, ϕVCL, ϕHCLK and ϕHCLR, and an output signal Vout in the order from top. In FIG. 5, a case in which the row <M> indicates rows <0> and <1> is illustrated regarding the drive signals ϕR and ϕT, and a case in which the column <N> indicates columns <0> and <1> and <2> is illustrated regarding the drive signal ϕHCLK.

As illustrated in FIG. 5, first, the clamp switch 253 is turned ON (the drive signal ϕVCL is High), the pixel resetting unit 236 is turned ON to a pulsed form (a pulsed drive signal ϕR<0> is High), and the transfer transistor 234 is turned OFF (a pulsed drive signal ϕT<0> is Low) such that a noise signal including a specific variation of the unit pixel 230 serving as a reading target and the noise at the time of pixel resetting is output from the unit pixel 230 to the vertical transfer line 239. At this time, the gate of the column source follower buffer 244 is set to a voltage of the clamp voltage Vclp by keeping the ON state of the clamp switch 253 (the drive signal ϕVCL is High). The clamp voltage Vclp is determined at a falling timing of the drive signal ϕVSH, and the reference voltage Vref is also determined at this timing.

Next, the transfer transistor 234 is turned ON in a pulsed form (the pulsed drive signal ϕT<0> is High) in a state in which the clamp switch 253 is turned OFF (the drive signal ϕVCL is Low) such that the signal, obtained by converting the charge photoelectrically converted by the photoelectric conversion element 231 using the charge converter 233, is read to the vertical transfer line 239. In this state, the imaging signal subjected to the voltage conversion is transferred to the vertical transfer line 239 by the charge converter 233. Through such an operation, an imaging signal (optical signal) from which the noise signal has been subtracted is output to the gate of the column source follower buffer 244 via the transfer capacitor 252. Here, the signal output to the gate of the column source follower buffer 244 is a signal sampled with reference to the clamp voltage Vclp.

The horizontal resetting transistor 256 is turned OFF (the drive signal ϕHCLR is Low) after sampling an imaging signal with reference to the clamp voltage Vclp, and the reset of the horizontal transfer line 258 is released.

Thereafter, the column selection switch 254 of the column <0> is turned ON (a pulsed drive signal φHCLK<0> is High) such that an imaging signal is transferred to the horizontal transfer line 258. At this time, the first sampling and holding switch 261b is turned ON in a pulsed form (a pulsed drive signal φHSH is High) such that an imaging signal is sampled by the first sampling capacitor 261c. Thereafter, the pulsed drive signal φMUXSEL (see FIG. 4) of a Low level is applied to the multiplexer 263 such that the imaging signal sampled by that the first sampling capacitor 261c is output to the output buffer 31. At this time, the horizontal resetting transistor 256 is turned ON (the pulsed drive signal φHCLR is High) in synchronization with the pulsed drive signal φMUXSEL of the multiplexer 263, and the horizontal transfer line 258 is reset again.

Continuously, the pulsed drive signal φMUXSEL (see FIG. 4) of a High level is applied to the multiplexer 263 such that the reference signal having a fluctuation component with the same phase as the imaging signal generated by the reference signal generating unit 248 is output to the output buffer 31, and further, the reset of the horizontal transfer line 258, which has been reset, is released by turning the horizontal resetting transistor 256 OFF (the drive signal φHCLR is Low), and the imaging signal is transferred to the horizontal transfer line 258 by turning the column selection switch 254 of the subsequent column ON (the drive signal φHCLK<1> is High). At this time, the first sampling and holding switch 261b is turned ON in a pulsed form (the pulsed drive signal φHSH (see FIG. 4) is High) such that an imaging signal is sampled by the first sampling capacitor 261c. Further, the horizontal resetting transistor 256 is turned ON (the drive signal φHCLR is High) such that the horizontal transfer line 258 is reset again, and further, the pulsed drive signal φMUXSEL (see FIG. 4) of the LOW level is applied to the multiplexer 263 in synchronization with the pulse of the horizontal resetting transistor 256 such that the sampled imaging signal is output to the output buffer 31.

When all the imaging signals of the row <0> are transferred to the horizontal transfer line 258, then, the transfer of the imaging signals of the row <0> is ended after setting the drive signal VSH and the drive signal φVCL to the High level, and the transfer of imaging signals of the next row <1> is started.

An imaging signal and a reference signal having a fluctuation component with the same phase as the imaging signal are alternately output from the output buffer 31 by repeating the above-described operation as many times as the number of columns of the light receiving unit 23 (or the number of columns that need to be read). When the read operation of one line is repeated as many times as the number of unit pixel rows (or the number of rows that need to be read), imaging signals of one frame are output.

According to the first embodiment described above, it is possible to alternately output an imaging signal and a reference signal having the fluctuation component with the same phase as the imaging signal for each pixel. In this manner, the reference signal (reference voltage Vref) having a fluctuation component with the same phase as a ripple component of the power supply, which is superimposed on the imaging signal output from the imaging signal generating unit 240, is output from the reference signal generating unit 248 so that it is possible to effectively eliminate the ripple component (noise component) superimposed during transmission of a signal using a subsequent circuit after the multiplexer 263, for example, a correlated double sampling circuit of the AFE unit 51 provided in the connector unit 5, and thus, it is possible to prevent degradation in image quality.

In addition, it is possible to suppress a variation (PVT variation: Process Voltage Temperature) in differential output voltage of an output level between an imaging signal and a reference signal in the darkness according to the first embodiment, and thus, it is possible to improve a yield ratio of the image sensor.

In addition, it is possible to improve a characteristic of a power supply rejection ratio (RSRP) according to the first embodiment.

Second Embodiment

Next, a second embodiment of the present invention will be described. An image sensor according to the second embodiment has a different configuration from the above-described image sensor (the imaging unit 20) according to the first embodiment. To be specific, a light receiving unit of the image sensor according to the second embodiment includes two photoelectric conversion elements, and these two photoelectric conversion elements are set as a unit pixel. Further, the reference signal generating unit of the photoelectric conversion element serving as a dummy pixel is not provided in the image sensor according to the second embodiment. Thus, only the configuration of the image sensor (imaging unit) according to the second embodiment will be described hereinafter. The same elements as those of the endoscopic system 1 according to the first embodiment will be denoted by the same reference signs and the explanation thereof will be omitted.

Configuration of First Chip

Figure 6:
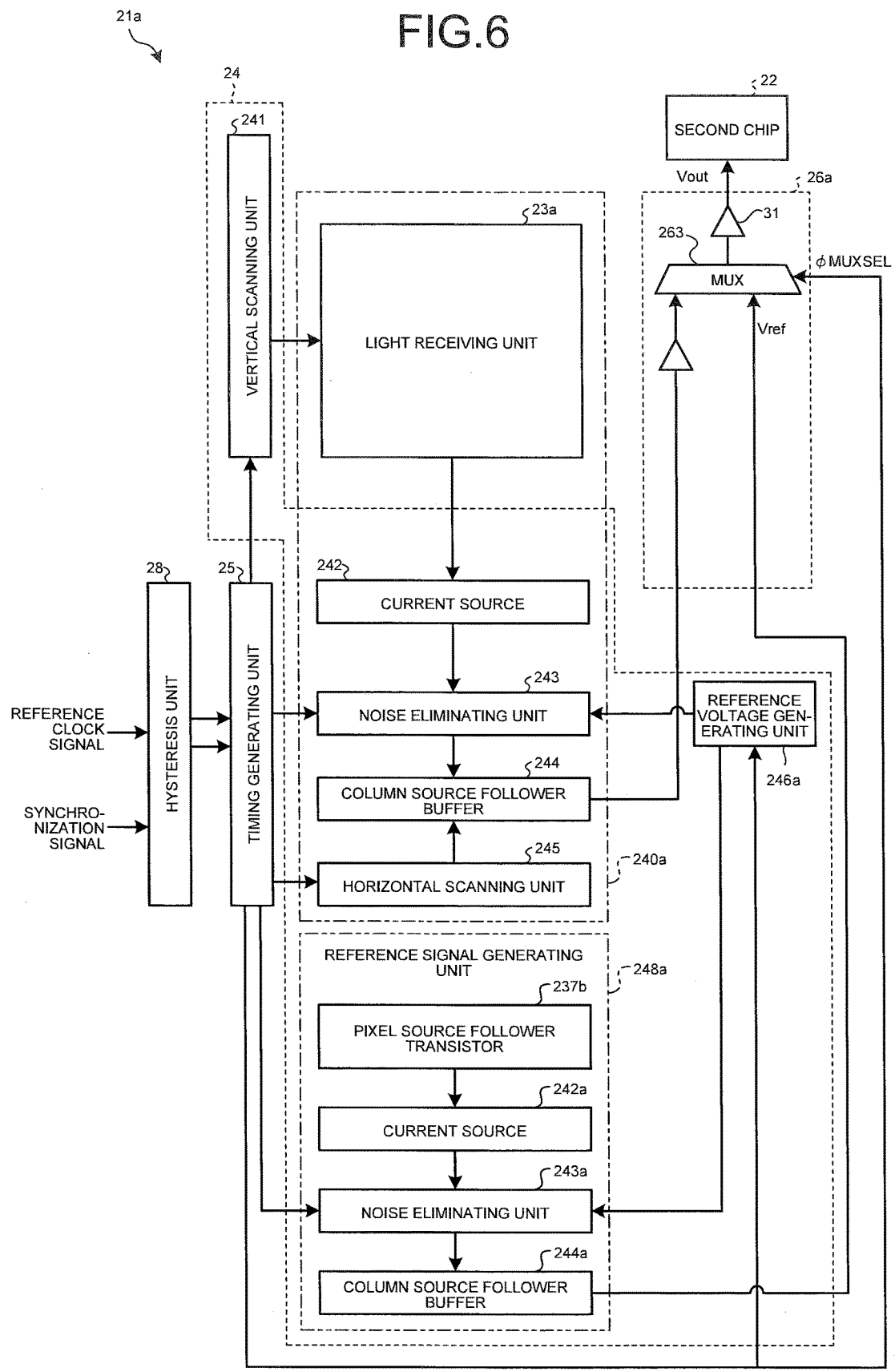
FIG. 6 is a block diagram illustrating a detailed configuration of a first chip of an imaging unit in an endoscopic system according to a second embodiment of the present invention.
Figure 7:
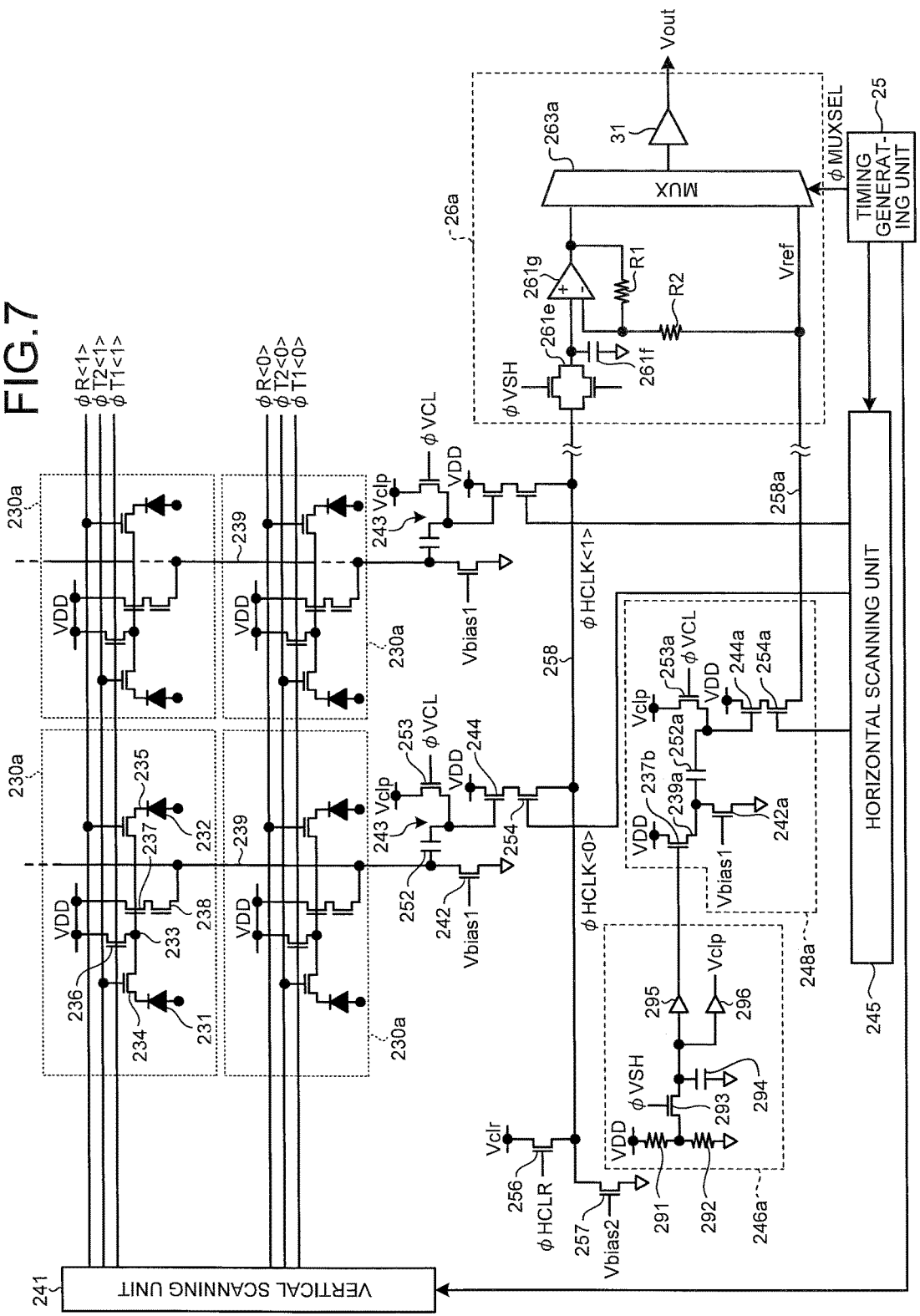
FIG. 7 is a circuit diagram illustrating the configuration of the first chip of the imaging unit in the endoscopic system according to the second embodiment of the present invention.

FIG. 6 is a block diagram illustrating a detailed configuration of a first chip of the imaging unit according to the second embodiment. FIG. 7 is a circuit diagram illustrating the detailed configuration of the first chip of the imaging unit according to the second embodiment.

As illustrated in FIGS. 6 and 7, a first chip 21a (image sensor) includes a light receiving unit 23a, a buffer 26a, a reference voltage generating unit 246a, and a reference signal generating unit 248a instead of the light receiving unit 23, the buffer 26, the reference voltage generating unit 246, and the reference signal generating unit 248 described above.

Multiple unit pixels 230a are arrayed in a two-dimensional matrix form in the light receiving unit 23a. Each of the unit pixels 230a includes the photoelectric conversion element 231, a photoelectric conversion element 232, the charge converter 233, the transfer transistor 234, a transfer transistor 235, the pixel resetting unit 236, the pixel source follower transistor 237, and a pixel output switch 238 (signal output unit). One or a plurality of the photoelectric conversion elements and the transfer transistor, which is configured to transfer a signal charge from each of the photoelectric conversion elements to the charge converter 233, are called a unit cell in the second embodiment. That is, the unit cell includes a set of one or the plurality of photoelectric conversion elements and the transfer transistor, and each of the unit pixels 230a includes one unit cell.

The photoelectric conversion element 232 photoelectrically converts incident light into a signal charge amount corresponding to the amount of light and accumulates the signal charge amount. The photoelectric conversion element 232 has a cathode side being connected to one end side of the transfer transistor 235 and an anode side being connected to a ground VDD.

The transfer transistor 235 transfers the charge from the photoelectric conversion element 232 to the charge converter 233. A gate of the transfer transistor 235 is connected to a signal line to which pulsed drive signals (row selection pulses) φT1 and φT2 are supplied, and the other end side thereof is connected to the charge converter 233. The transfer transistor 235 is turned into an ON state when the pulsed drive signals φT1 and φT2 are supplied to the transfer transistor 235 from the vertical scanning unit 241 via the signal line, and transfers the signal charge from the photoelectric conversion element 232 to the charge converter 233.

The reference signal generating unit 248*a* is connected to the dedicated vertical transfer line 239*a* separately from a column of the unit pixel 230*a*. The reference signal generating unit 248*a* includes a circuit that generates a reference signal having a fluctuation component with the same phase as a fluctuation component of the power supply existing in the output signal (imaging signal) to be formed by an imaging signal generating unit 240*a*. The reference signal generating unit 248*a* includes a circuit which has a structure equivalent to at least one or more of a plurality of circuits constituting a video signal system circuit.

Here, a detailed configuration of the reference signal generating unit 248*a* will be described. The reference signal generating unit 248*a* is not provided with the photoelectric conversion element 231*a* (dummy photodiode), the charge converter 233*a*, the transfer transistor 234*a*, and the pixel resetting unit 236*a* as compared to the above-described circuit configuration of the reference signal generating unit 248. To be specific, the reference signal generating unit 248*a* includes a pixel source follower transistor 237*b*, the current source 242*a*, the noise eliminating unit 243*a*, the column source follower buffer 244*a*, and the column selection switch 254*a*.

The pixel source follower transistor 237*b* has the same configuration as the above-described pixel source follower transistor 237. The pixel source follower transistor 237*b* has one end side being connected to the power-supply voltage VDD and the other end side being connected to the vertical transfer line 239*a*, and the reference signal voltage Vfd_H is input to a gate thereof from the reference voltage generating unit 246*a*.

The reference voltage generating unit 246*a* includes the resistance voltage dividing circuit, formed of the two resistance 291 and resistance 292, the switch 293 driven using the drive signal φVSH, the sampling capacitor 294, the operational amplifier 295, and the operational amplifier 296. The reference voltage generating unit 246*a* generates the reference signal voltage Vfd_H from the power-supply voltage VDD and the clamp voltage Vclp of the noise eliminating unit 243 at the timing that the drive signal φVSH is driven by driving of the switch 293.

The buffer 26*a* holds the imaging signal input from the horizontal transfer line 258 and the reference signal input from the horizontal transfer line 258*a* individually, and outputs the imaging signal and the reference signal to the second chip 22 in a sequentially switched manner based on a signal (drive signal φMUXSEL) input from the timing generating unit 25.

Here, a detailed configuration of the buffer 26*a* will be described. The buffer 26*a* includes a sampling and holding switch 261*e*, a sampling capacitor 261*f*, an operational amplifier 261*g*, a multiplexer 263*a*, and the output buffer 31.

The sampling and holding switch 261*e* has one end side being connected to the horizontal transfer line 258 and the other end side being connected to an input side (plus terminal) of the first operational amplifier 261*g*, and a signal line to which the drive signal φVSH is supplied is connected to the gate.

The sampling capacitor 261*f* has one end side being connected to the other end side of the sampling and holding switch 261*e* and the other end side being connected to the ground GND. The sampling capacitor 261*f* holds a voltage immediately before the sampling and holding switch 261*e* is turned into an ON state, and outputs the voltage held immediately before the sampling and holding switch 261*e* is turned into the ON state to the multiplexer 263*a* while the sampling and holding switch 261*e* is in an OFF state.

The input side (plus terminal) of the operational amplifier 261*g* is connected to the other end side of the sampling and holding switch 261*e*, and an output side thereof is connected to the multiplexer 263*a*. In addition, the output of the operational amplifier 261*g* is input to an inverting input terminal (minus terminal) of the operational amplifier 261*g* via the resistance R1. Further, the reference signal (reference voltage Vref) is input to the inverting input terminal (minus terminal) of the operational amplifier 261*g* from the reference signal generating unit 248*a* via the resistance R2.

The multiplexer 263*a* outputs the imaging signal input from the operational amplifier 261*g* and the reference signal (reference voltage Vref) input from the reference signal generating unit 248*a* via the horizontal transfer line 258*a* to the output buffer 31 in a switched manner based on the drive signal φMUXSEL input from the timing generating unit 25.

The first chip 21*a* of the imaging unit 20 configured as above performs the same operation as in the first embodiment described above, and alternately outputs the imaging signal and the reference signal (reference voltage Vref) to the output buffer 31 for each pixel. In this manner, it is possible to alternately output the reference signal (reference voltage Vref), which has the same power supply ripple as a power supply ripple that is superimposed on the imaging signal output from the imaging signal generating unit 240*a*, from the reference signal generating unit 248*a*, and thus, it is possible to effectively eliminate the ripple noise superimposed during transmission of a signal using a subsequent circuit after the multiplexer 263*a*, for example, a correlated double sampling circuit provided in the connector unit 5.

According to the second embodiment described above, it is possible to alternately output the video signal and the reference signal for each pixel. In this manner, it is possible to effectively eliminate the ripple noise superimposed during the transmission of the signal using the subsequent circuit after the multiplexer 263*a*, for example, the correlated double sampling circuit provided in the connector unit 5 by alternately outputting the reference signal (reference voltage Vref), which has the same power supply ripple as a ripple component of the power supply that is superimposed on the imaging signal output from the imaging signal generating unit 240*a*, from the reference signal generating unit 248*a*, and thus, it is possible to effectively prevent the degradation in image quality.

In addition, according to the second embodiment, the reference signal generating unit 248*a* is configured only of the pixel source follower transistor 237*b*, the current source 242*a*, the noise eliminating unit 243*a*, and the column source follower buffer 244*a*, and is not provided with the photoelectric conversion element 231*a*, and thus, it is possible to reduce an area of the first chip 21*a* as compared to the first embodiment described above.

In the present invention, the reference signal generating unit may include at least an output circuit having a structure equivalent to the output circuit. To be specific, the reference signal generating unit may include the column source follower buffer 244 and the column selection switch 254 which have been described above in the first and second embodiments.

According to some embodiments, it is possible to prevent the degradation of the image quality.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image sensor comprising:
a plurality of photoelectric conversion pixels arranged in a two-dimensional matrix form, each of the plurality of photoelectric conversion pixels being configured to receive light from outside and accumulate a charge corresponding to an amount of received light;
an imaging signal generator comprising:
a conversion circuit configured to convert the charge accumulated in each of the plurality of pixels into an imaging signal;
a noise eliminating circuit configured to eliminate a noise component included in the imaging signal; and
an output circuit configured to output the imaging signal from the conversion circuit; and
a reference signal generator comprising a circuit having a same structure as that of at least one of the conversion circuit, the noise eliminating circuit, and the output circuit of the imaging signal, the circuit included in the reference signal generator being configured to generate a reference signal having a fluctuation component with a same phase as the imaging signal generated by the imaging signal generator.

2. The image sensor according to claim 1, wherein the reference signal generator comprises the circuit having the same structure as that of the conversion circuit.

3. The image sensor according to claim 1, wherein the reference signal generator comprises circuits having same structures as those of the conversion circuit, the noise eliminating circuit, and the output circuit.

4. The image sensor according to claim 1, wherein the reference signal generator comprises the circuit having the same structure as that of the output circuit.

5. The image sensor according to claim 1, wherein the conversion circuit comprises at least a pixel source follower circuit configured to convert the charge from each of the photoelectric conversion pixels into the imaging signal.

6. An imaging device comprising the image sensor according to claim 1.

7. An endoscope comprising the imaging device according to claim 6 at a distal end side of an insertion portion.

8. An endoscopic system comprising:
the endoscope according to claim 7; and
a controller configured to perform conversion into an image signal using the imaging signal and the reference signal.

9. The image sensor according to claim 1, further comprising:
a buffer configured to hold the imaging signal output from the output circuit and the reference signal generated by the reference signal generator and alternately output the held imaging signal and the held reference signal.

* * * * *